United States Patent [19]

Daniels et al.

[11] Patent Number: 5,108,755
[45] Date of Patent: Apr. 28, 1992

[54] BIODEGRADABLE COMPOSITES FOR INTERNAL MEDICAL USE

[75] Inventors: Alma U. Daniels, Salt Lake City, Utah; Jorge Heller, Woodside, Calif.

[73] Assignees: SRI International, Menlo Park, Calif.; University of Utah, Salt Lake City, Utah

[21] Appl. No.: 345,034

[22] Filed: Apr. 27, 1989

[51] Int. Cl.⁵ .............................................. A61F 2/00
[52] U.S. Cl. ................................... 424/426; 524/417; 424/78.37
[58] Field of Search ................... 424/426, 78; 524/417

[56] References Cited

U.S. PATENT DOCUMENTS

| | | | |
|---|---|---|---|
| 3,640,741 | 2/1972 | Etes | 424/426 X |
| 3,739,773 | 6/1973 | Schmitt | 424/426 |
| 4,093,709 | 6/1978 | Choi et al. | 424/426 X |
| 4,096,239 | 6/1978 | Katz et al. | 424/426 |
| 4,304,767 | 12/1981 | Heller et al. | 424/78 |
| 4,346,028 | 8/1982 | Griffith | 524/417 |
| 4,513,143 | 4/1985 | Ng et al. | 549/335 |
| 4,532,335 | 7/1985 | Helwing | 549/335 |
| 4,639,366 | 1/1987 | Heller | 424/484 |
| 4,717,487 | 1/1988 | Griffith et al. | 252/1 |
| 4,764,364 | 8/1988 | Heller et al. | 424/78 |
| 4,786,664 | 11/1988 | Yates | 524/417 |

FOREIGN PATENT DOCUMENTS

| | | |
|---|---|---|
| 0031223 | 7/1981 | European Pat. Off. |
| 0146398 | 6/1985 | European Pat. Off. |
| 2169914 | 7/1986 | United Kingdom |

Primary Examiner—Thurman K. Page
Assistant Examiner—William E. Benston
Attorney, Agent, or Firm—Morrison & Foerster

[57] ABSTRACT

A family of composites suitable for use as materials of construction for implantable medical devices is disclosed. In the most preferred embodiment, the substrate polymer is an ortho ester polymer formed by the reaction of a ketene acetal having a functionality of two or more with a polyol. Also in the most preferred embodiment, the reinforcement material in the composites is calcium-sodium metaphosphate ("CSM") fibers. In other embodiments, the composites may replace either (but not both) of the substrate or the reinforcement with materials of the art.

10 Claims, 5 Drawing Sheets

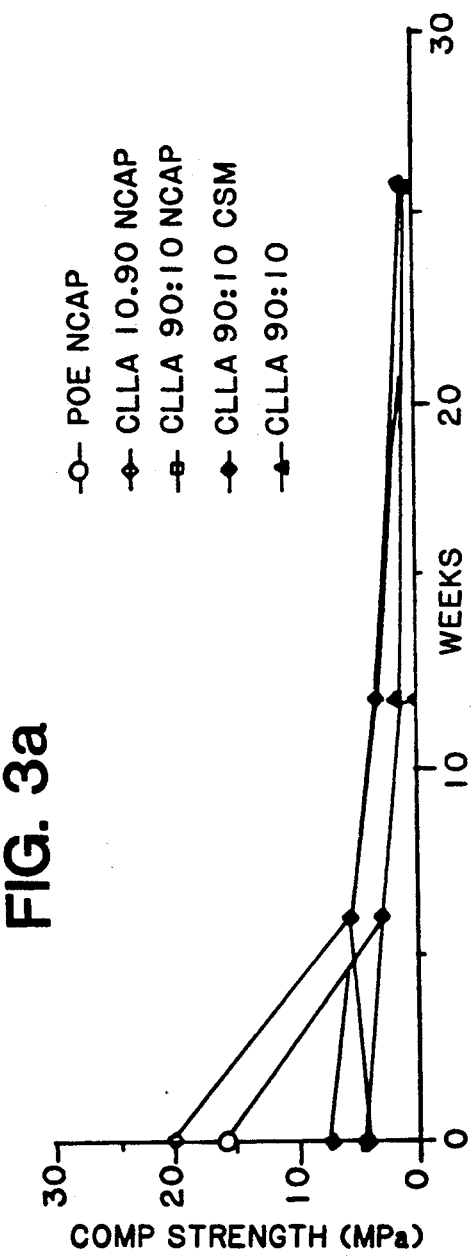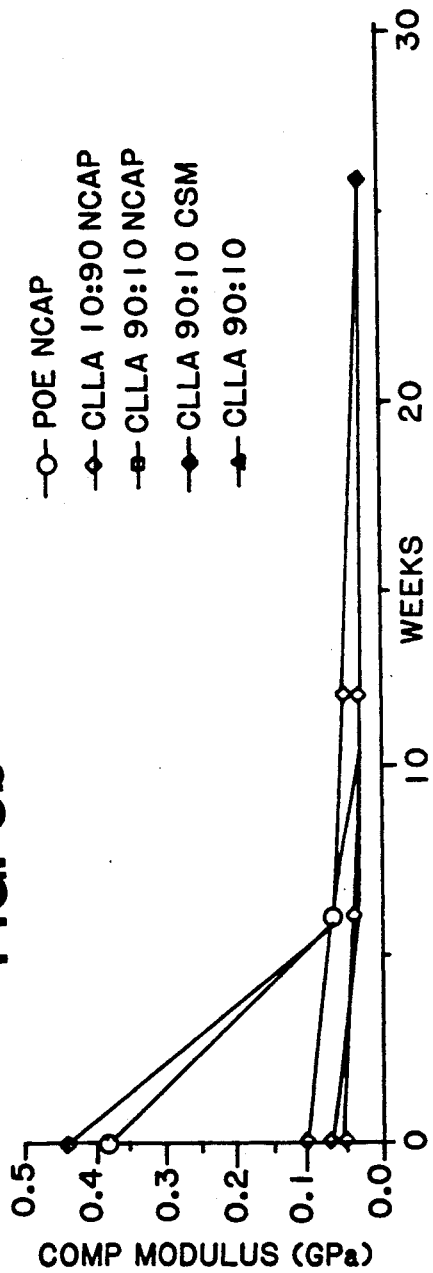

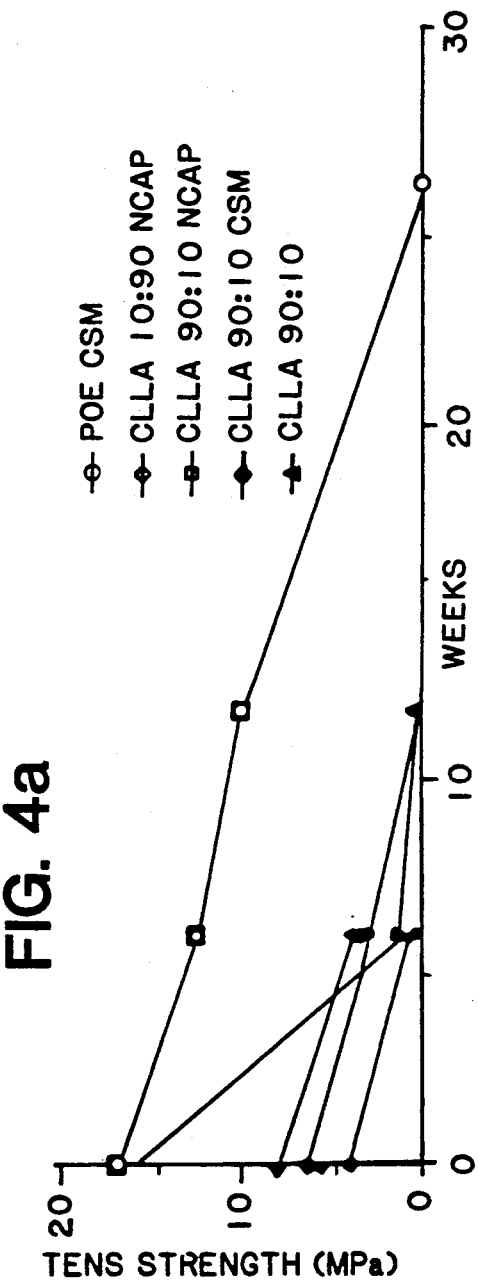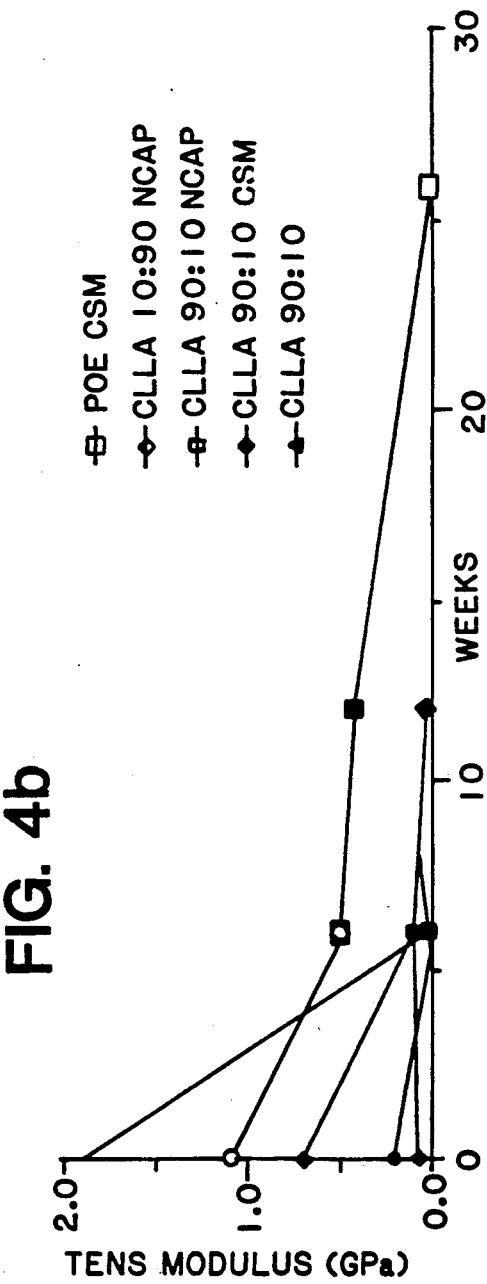
FIG. 4a
FIG. 4b

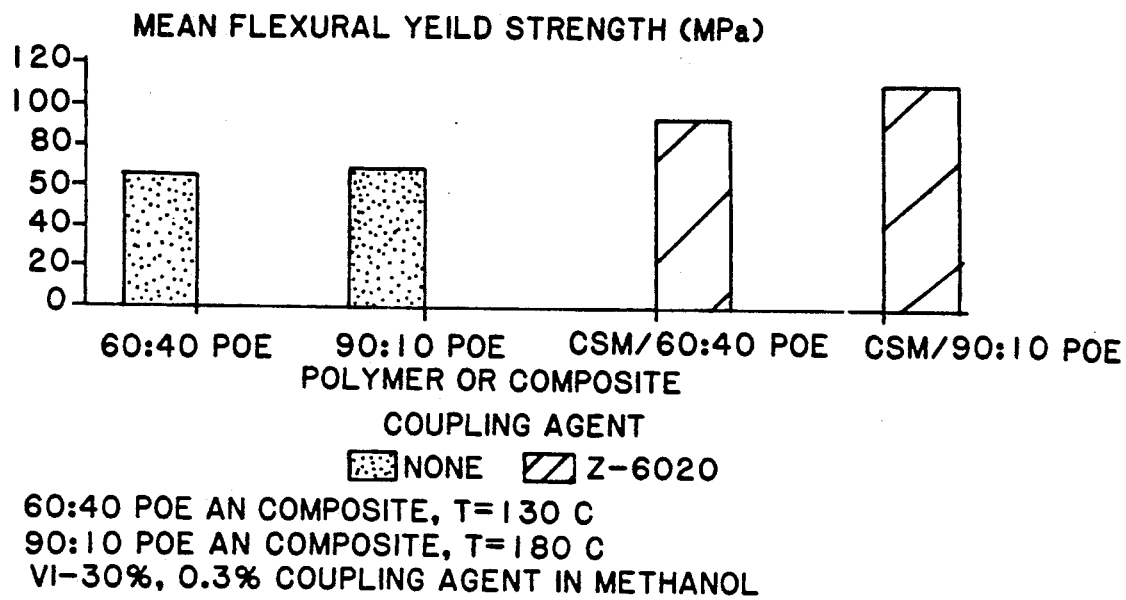
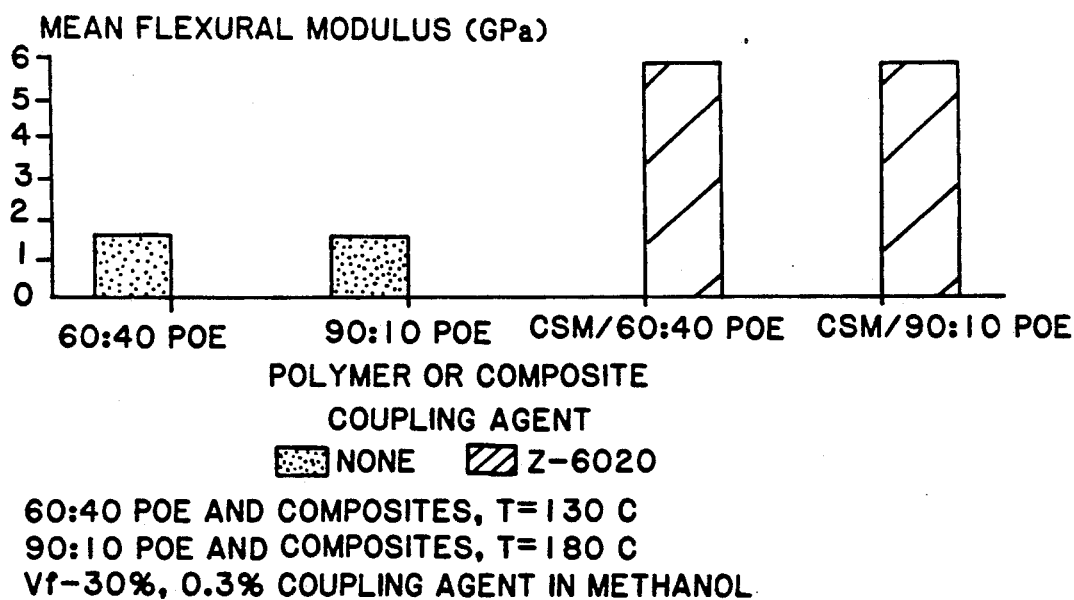

Vf-30%. 0.3% COUPLING AGENT IN METHANOL

Vf-30%, 0.3% COUPLING AGENT IN METHANOL

BIODEGRADABLE COMPOSITES FOR INTERNAL MEDICAL USE

BACKGROUND OF THE INVENTION

1. Field of the Invention

This invention relates to biodegradable composites for internal use. That is, it relates to composites made up of biodegradable substrate and a biodegradable reinforcement which can be used internally in the body of a human or animal for bone fixation or the like. In this use, the composites gradually completely degrade to soluble products. In preferred embodiments, this invention relates to the use of poly(ortho esters) as the erodible substrate and to the use of calcium-sodium metaphosphate fibers as the reinforcement in such composites.

2. Introduction and Summary of Background Art

Metal plates, pins, rods, and screws are used for rigid internal fixation of bones and tendons which have been damaged by trauma or reconfigured surgically to correct defects occurring congenitally, developmentally or as the result of disease. These devices are most commonly fabricated from stainless steel and align bone fragments by bringing their edges into close proximity. Due to device structural stiffness they control relative motion to allow bone union. For healing, the stabilization must persist for several weeks or months without device breakage or loosening. While the level of relative motion that can be tolerated has not been thoroughly determined, it is understood that gross motion at the fracture site will result in non-union of the bone fragments.

While metal devices of the type well known in the art can hold fragments in close proximity, they may at times interfere with proper healing. This has been traced to their extreme rigidity. It has been demonstrated that completion of healing is prevented by permanent highly rigid fixation of the bone fragments. This is because much of the load that is normally carried by the bone is transferred across the fracture site by the implant. This load transfer is brought about by a mismatch between the elastic modulus of the bone and the metal implant $E_{bone} = 6$–$20$ Gpa and $E_{metal} = 100$–$200$ Gpa). The stress-shielded bone heals incompletely or may even remodel so that the shielded area is susceptible to refracture when the implant is removed.

Another problem inherent in the metal fixation implants used heretofore is that they generally need to be surgically removed after they have served their desired function. This is done to eliminate pain (which can be caused by local corrosion, tissue pressure or friction related to loosening), or at the suggestion of the surgeon where he or she believes this represents the patient's best interest. This removal involves a second surgery, with its attendant costs and risks.

Some attempts at reducing the rigidity of fixation implants have included the use of permanent implants made from titanium alloys, polymers and carbon-reinforced polymers such as nylon, polyether sulphone and polymethylmethacrylate. These implants lessen stress shielding but still may need to be removed after the bone heals.

Beginning in 1971, investigators reported the possibility of employing implants fabricated from materials which gradually break down or dissolve when placed in the body. An implant formed of a biodegradable material, which meets basic design criteria, including biocompatibility (sterilizability and low toxicity), compatibility for intraoperative reshaping (where needed) and sufficient initial strength and stiffness, has two major advantages over conventional implants: (a) It allows gradual load transfer to the healing bone as it degrades and (b) It eliminates the need for surgical removal.

The earliest reported use of an resorbable polymer for fracture fixation was described by Kulkarni et al. in the *J. Mater. Res.* 5, pp. 169–181 (1971). He successfully used extruded rods of poly(lactic acid) to reduce mandibular fractures in dogs.

More recently the number of reports dealing with the use of biodegradable polymers and composites for fracture fixation has increased dramatically. At least 63 articles on the subject have appeared as of the date of this application. The most common materials of construction for these articles are poly(lactic acid) and poly(glycolic acid). Other materials also have been used. Typical references in the literature and the materials they describe include:

H. Alexander et al. "Development of new methods for phalangeal fracture fixation," *J. Biomech.*, 14(6), pp. 377–387 (1981) - poly(levo lactic acid) "PLLA" rods;

P. Christel et al. "Biodegradable composites for internal fixation," in *Advances in Biomaterials* 3, *Biomaterials* 1980, ed. G. D. Winter et al. 3, 1982, pp. 271–280 - combinations of poly(d/l lactic acid) "PDLLA" and PLLA, as well as polyglycolic acid "PGA";

M. Vert et al. "Bioresorbable plastic materials for bone surgery," *Macromolecular Biomaterials* ed. Hastings et al. 1984, pp. 120–142 - combinations of "PDLLA" and PLLA;

D. Lewis et al. "Absorbable fixation plates with fiber reinforcement", *Trans. Soc. Biomater.*, 4, p. 61 (1981) - PDLLA reinforced with alumina, alumina-boriasilica and carbon;

J. Kilpikari et al "Carbon fibre reinforced biodegradable and non-biodegradable polymers as bone plate materials," *Trans. Soc. Biomater.*, 7, p. 242 (1984) - PGA/PLA copolymers with and without carbon reinforcement;

L. Claes et al. "Refixation of osteochondral fragments with resorbable polydioxanone pins in animal experiments", *Trans. Soc. Biomater.*, 8, p. 163 (1985) - the poly(ethyl ether) polydioxanone;

R. H. Wehrenberg, "Lactic acid polymers: strong, degradable thermoplastics," *Mater. Eng.*, 94 (3), pp. 63–66 (1981) - copolymers of L-lactide and epsilon-caprolactone, as well as polycaprolactone "PCL";

X. D. Feng et al. "Synthesis and evaluation of biodegradable block copolymers of epsilon-caprolactone and d,l-lactide," *J. Polym. Sci.: Polym. Letters Ed.*, 21, pp. 593–600 (1983) - PCL and various PCL/PDLLA copolymers;

V. Sknondia et al. "Chemical and physicomechanical aspects of biocompatible orthopedic polymer (BOP) in bone surgery," *J. Int. Med. Res.*, 15 (5), pp. 293–302 (1987) - N-vinylpyrollidone/methylmethacrylate copolymers;

A. C. Ibay et al. "Synthesis and properties of polymers for biodegradable implants," *Polym. Mater. Sci. Eng.*, 53, pp. 505–507 (1985)- polypropylene fumarate;

J. Kohn et al. "Poly(iminocarbonates) as potential biomaterials." *Biomaterials*, 7(3), pp. 176–182 (1986) - polyiminocarbonate;

A. J. Owen, "Some dynamic mechanical properties of microbially produced poly-beta-hydroxybutyrate/- betahydroxyvalerate copolymers," *Colloid & Polymer Science*, 263, pp. 799–803 (1985), among several - copolymers of polyhydroxybutrate/polyhydroxyvalerate;

S. W. Shalaby et al. "Absorbable polyesters with structure modulated biological properties," *Trans. Soc. Biomater.*, 8, p. 212 (1985) - polyalkylene oxalates; and L. Claes et. al. "Resorbable implants for the treatment of bone defects," *Trans. Soc. Biomater.*, 11, p. 499 (1988) - polyester-amide.

Typical fibers used as reinforcements in these composites are carbon fibers and other nondegradable materials, biodegradable inorganic polymers and biodegradable organic polymers. Some of the reinforcements used in these prior studies have been nonerodible—for example, carbon fibers, glass filaments and the like. While these materials can give dramatic increases in initial strength to composites over their polymer matrix alone they have the medically unacceptable problem of leaving behind finely divided nondegradable debris when the substrate disappears and also sometimes giving rise to rapid losses of strength during environmental exposure. Typical biodegradable polymers include self-reinforcement where the reinforcement is made of polymers of the same material as the polymer matrix but with the reinforcing polymer having a high degree of orientation of polymer chains for increased strength. In other cases one organic material, for example poly(glycolic acid) fibers, can be used in another organic material such as poly(lactic acid).

While the advantages of biodegradable supports are quite clear, especially their elimination of the need to perform a second surgical procedure to remove them, there are still advances to be made. A major area of interest involves identifying materials which have a proper balance of strength and bioerosion.

This balance is a fine one. For example, much of the work carried out heretofore has focused on PLLA and PDLLA. These two materials, while chemically closely related, with one a pure material and the other a mixture of two enantiomers of the same compound, illustrate the balance point. Pure PLLA is quite strong, having a tensile strength of about 60 MPa in one type of test. PDLLA has a tensile strength of about 40 MPa in the same test, with copolymers falling between these two values. Thus, one could achieve different levels of strength by varying the ratio of the comonomer units. The erosion properties of these materials also vary as a function of composition. Pure PLLA is very durable, or nondegradable, depending on the user's point of view. It retains nearly all of its physical integrity after 150 days of implantation. The same study reported that a 50—50 PLLA-PDLLA copolymer degraded to 31% of its initial strength in 30 days of implantation. Many workers in the field have looked at the physical and erosion properties of erodible or degradable polymers, each seeking a composite system which will have physical support properties which lead to optimal healing and degradation properties which lead to prompt clearance of the implant from the system without any premature degradation which would compromise the desired physical properties.

STATEMENT OF THE INVENTION

We now have found a family of composites which offer substantial promise as materials of construction for implantable devices. In the most preferred embodiment, the substrate polymer is an ortho ester formed by the reaction of a ketene acetal having a functionality of two or more with a polyol, which term includes alcohols and phenols. Also in the most preferred embodiment, the reinforcement material in the composites is calcium-sodium metaphosphate ("CSM") fibers.

Thus, in one aspect this invention concerns implantable composites made from these two materials.

In another aspect, this invention concerns implantable composites fabricated from these ortho ester substrate polymers and an erodible reinforcement, generally.

In a further aspect, this invention concerns implantable composites fabricated from the CSM fiber materials and erodible substrates of the art.

In yet another aspect, this invention concerns implantable reinforcement devices fabricated from these materials.

In yet a further aspect, this invention relates to a method of treating the CSM fibers, and the product thereof to make them more compatible with the poly(ortho ester) substrates.

DETAILED DESCRIPTION OF THE INVENTION

Brief Description of the Drawings

This invention will be described with reference being made to the appended drawings. In these drawings

FIG. 3a is a graph illustrating the degradation of certain composites of this invention as well as materials not in accord with this invention in simulated internal media as determined by measuring compressive strength;

FIG. 3b is a graph illustrating the degradation of certain composites of this invention as well as materials not in accord with this invention in simulated internal media as determined by measuring compressive modulus;

FIG. 4a is a graph illustrating the degradation of certain composites of this invention as well as materials not in accord with this invention in simulated internal media as determined by measuring tensile strength;

FIG. 4b is a graph illustrating the degradation of certain composites of this invention as well as materials not in accord with this invention in simulated internal media as determined by measuring tensile modulus;

FIGS. 5a and 5b are bar graphs illustrating the improvement in properties of POE materials achieved with reinforcement.

Definitions

Figure 1:
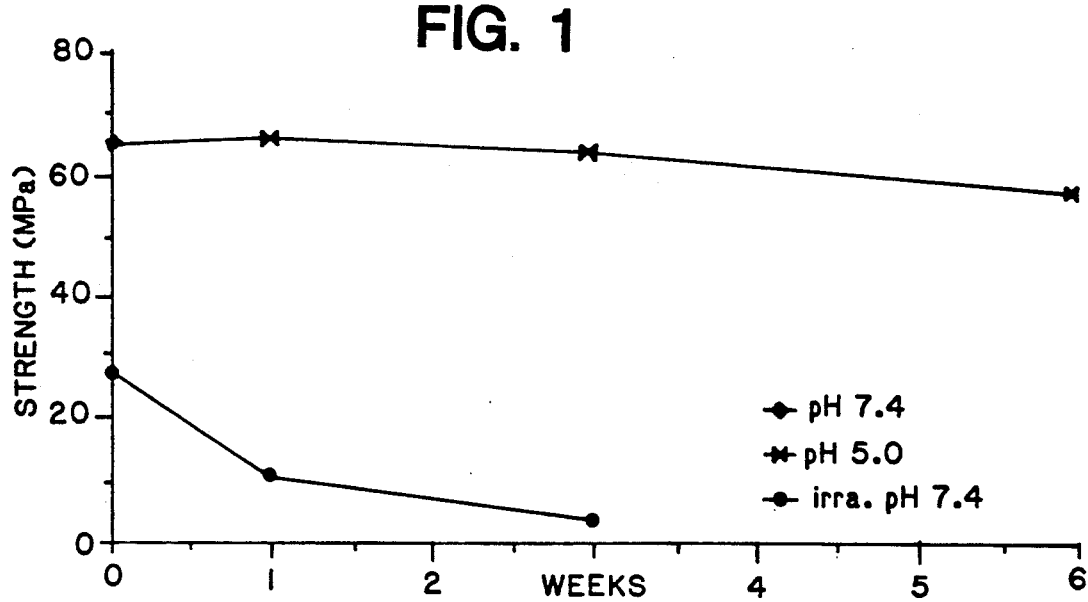
FIG. 1 is a graph illustrating the degradation of certain composites of this invention in simulated internal media as determined by measuring flexural strength.

This invention involves bioerodible composites. The terms "degradable", "erodible", "absorbable", and "resorbable" are used somewhat interchangeably in the literature of this field, with or without the prefix "bio". In this application, these terms will be used interchangeably to describe materials broken down and gradually absorbed or eliminated by the body, whether degradation is due mainly to hydrolysis or mediated by metabolic processes.

Ortho Ester Substrates

One preferred group of substrate materials for use in the composites of this invention are the poly(ortho ester) materials formed from ketene acetals and polyols. These materials are described in U.S. Pat. No. 4,304,767. This patent is incorporated herein by reference. These ortho ester polymers have repeating mer units represented by the general formulas:

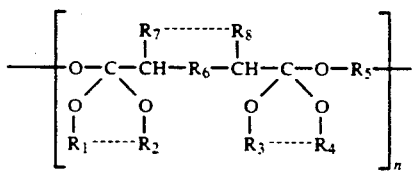

wherein n is an integer substantially greater than 10; wherein $R_1$, $R_2$, $R_3$ and $R_4$ are the same or different essentially hydrocarbon groups, $R_1$ and $R_2$ being separate groups or parts of a cyclic group and $R_3$ and $R_4$ being separate groups or parts of a cyclic group; $R_5$ is an essentially hydrocarbon group which is the residue of a polyol $R_5(OH)_n$ wherein n is an integer equal to two or more, such polyol being a single molecular species or a mixture of molecular species; $R_6$ is a valence bond or an essentially hydrocarbon group; $R_7$ and $R_8$ are hydrogen or essentially hydrocarbon groups which may be separate groups or may form parts of a cyclic group; and wherein such linear chains may be crosslinked to similar chains and

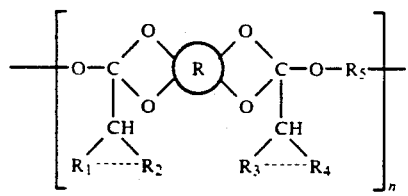

wherein n is an integer substantially greater than 10; wherein $R_1$ and $R_2$ are hydrogen or the same or different essentially hydrocarbon groups and may be separate groups or may form parts of a cyclic group; ⓡ is a quadrivalent organic grouping; $R_3$ and $R_4$ are hydrogen or the same or different essentially hydrocarbon groups and may be separate groups or may form parts of a cyclic group; $R_5$ is an essentially hydrocarbon group which is the residue of a polyol $R_5(OH)_a$ wherein a is an integer equal to two or more, such polyol being a single molecular species or a mixture of molecular species; and wherein such linear chain may be crosslinked with other similar chains.

These ortho ester polymers are preferably formed by a condensation reaction between ketene acetals having a functionality of two or more and hydroxyl compounds having a functionality of two or more. The term "functionality", as applied to a ketene acetal, is meant a ketene acetal group

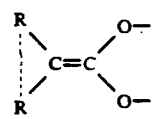

-continued
or

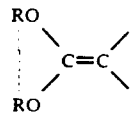

Thus, a di-ketene acetal has a functionality of two, a tri-ketene acetal has a functionality of three, etc. Similarly, where the term "functionality" is used in connection with a polyol, it refers to the hydroxyl groups present in the polyol.

The ketene acetals are of two types.

The first is as follows:

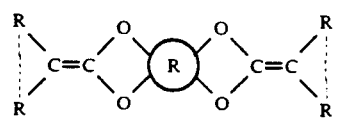

Type I Monomers wherein the terminal R groups are the same or different, and can be H or essentially hydrocarbon groups, primarily alkyl, aryl, cycloaliphatic or aralkyl groups, and may be saturated or unsaturated, and R is a quadravalent grouping or atom.

By "essentially hydrocarbon" is meant that the groups R may contain hetero atoms provided they do not inhibit polymerization with a polyol to an unacceptable degree, do not inhibit degradation of the polymer to an unacceptable degree and do not give rise to toxic or difficultly metabolizable degradation products. The formulation R-R indicates that the two R groups may be joined together to form a cyclic group or may be separate unconnected groups.

The second type of ketene acetal is as follows:

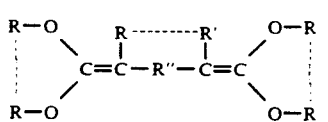

Type II Monomers wherein the terminal R groups are the same or different essentially hydrocarbon groups, the R' groups are hydrogen or essentially hydrocarbon groups and R" is a bivalent organic grouping which is also essentially hydrocarbon.

The Type I monomers condense with diols HO—R—OH, R being an essentially hydrocarbon, to produce linear polymers as follows:

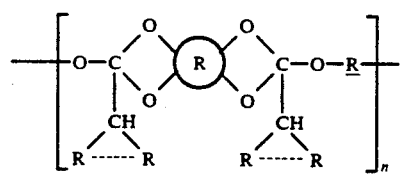

wherein R is derived from the polyol and n is an integer greater than one and usually 100 to 300 or greater.

The Type II monomers polymerize with diols to produce linear polymers as follows:

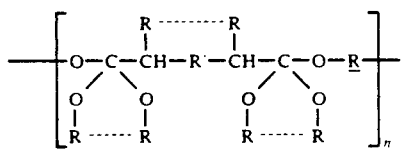

where R and n are similarly defined.

It will be understood that where the polyol and/or the ketene acetal has or have functionalities greater than two, crosslinked polymers will result. As noted below crosslinking may also be achieved by other crosslinking agents.

Certain of the diketene acetals which can be used in the present invention are described in Table I.

TABLE I

Structures of Ketene Acetals of Type I

| | |
|---|---|
| (structure) | Compound I |
| (structure) | Compound II |
| (structure) | Compound III |
| (structure) | Compound IV |
| (structure) | Compound V |
| (structure) | Compound VI |

Structures of Ketene Acetals of Type II

| | |
|---|---|
| (structure) | Compound VII |
| (structure) | Compound VIII |
| (structure) | Compound IX |
| (structure) | Compound X |

Exemplary polyols suitable as reactants include diols, triols, and the like that can enter into the polymerization reaction without adversely affecting it or the polymeric product. The polyols are known to the art in reported synthesis and they are commercially available. Generally, they include aliphatic diols, triols and the like of the straight or branched chain type. Representative polyols are alkane polyols having a terminal hydroxyl group at the terminus of an alkylene chain of the formula $$HO-R-OH$$
$$|$$
$$(OH)_y$$

wherein R is an alkylene chain of 2 to 12 carbon atoms and y is 0 to 6. Typical diols, named as the glycols, include 1,2-propylene glycol, 1,5-pentylene glycol, 3,6-diethyl-1,9-nonylene glycol, trans-cyclohexanedimethanol and the like.

Polyols containing more than 2 reactive hydroxyl radicals suitable for use herein include polyhydroxyl compounds such as 1,2,3,4,5,6-hexanehexol; 1,2,3-propanetriol; 1,5,12-dodecanetriol; 1,2,6-hexanetriol and the like.

Other polyols suitable for synthesizing the poly(ortho esters) include polyglycols containing a repeating glycol monoether moiety $-OCH_2(CH_2)_pOH$ wherein p is 1 to 5.

Additional polyols that can be used in the poly(ortho esters) are polyhydroxyl compounds having 2 or more reactive hydroxyl groups such as pentaerythritol and dipentaerythritol.

Also phenolic polyols (two or more phenolic hydroxyl groups) and mixed phenolic-alcoholic polyols may be employed. Also mixtures of two or more polyols may be employed Examples of polyols and of mixed phenoloic-alcoholic polyols are as follows: 4,4'-isipropylidenediphenol (bisphenol A); 4-hydroxybenzylalcohol; and non-phenolic polyols having aromatic linking groups between the hydroxyl groups, e.g. 1,4-dihydroxymethylbenzene. Furthermore, tri- (and higher) hydric phenols may be used such as pyrogallol; hydroxyhydroquinone; phloruglucinol; and propyl gallate.

Other Substrate Polymers

In some embodiments of this invention the composites may include substrate polymers other than the above-described ortho esters. These substrate materials include poly(lactic acid) including "PLLA", "PDLLA" and combinations of "PLLA" and "PDLLA"; poly(glycolic acid) ("PGA") copolymers of L-lactide and epsilon-caprolactone; polycaprolactone ("PCL"); PCL/PDLLA copolymers; polypropylene fumarate; polyiminocarbonate; copolymers of polyhydroxybutrate/polyhydroxyvalerate; poly(alkylene oxalates); poly(ester-amide) and the polyanhydrides described by K. W. Leong et al., J. Biomed. Res. Vol 19 pp. 941-955, (1985) incorporated by reference. These alternate substrate materials are described in the references included in the Background section of this application which references are incorporated herein by reference.

The CSM Reinforcements

In certain embodiments, the composites of this invention employ calcium-sodium-methaphosphate ("CSM") fibers as reinforcements. CSM is described in the U.S. Pat. No. 4,346,028, which patent is herein incorporated by reference. This patent teaches the preparation and use of asbestiform calcium-sodium-methaphosphate ("CSM") crystals as reinforcement-filler materials. This material has been promoted by and is available as a developmental scale chemical from Monsanto Company (St. Louis, Mo.) and has been proposed as use as a reinforcer and filler in flooring and roofing materials, friction materials, plastic materials, plastics, resins and elastomers, insulating materials and biomedical materials. The use of these materials in erodible composites for internal medical use is, to our understanding, not disclosed in the literature.

The CSM materials were proposed as an alternative to asbestos. As described by Bruce Monzyk in September-October 1986, Plastics Compounding, pp. 42-46, this material was developed as an insoluble fiber that would degrade naturally if ingested or inhaled. This material, an inorganic covalently bonded polyphosphate having sodium and calcium cations adjacent to and ionically bonded to the polymer can generally be used as distributed by Monsanto. However, when used in combination with the orthoesters, this material may lead to premature breakdown of the orthoester because it tends to have an acidic surface. This can be easily prevented by blocking some of the acidic functions on the raw fiber such as by treating with a silylating agent as will be demonstrated in the preparation section.

The composites of this invention contain at least two materials: a substrate polymer and a fibrous reinforcement. The amount of reinforcement should be an effective reinforcing amount or level. An "effective reinforcing" amount is such as to not be so great as to destroy the continuous phase presented by the polymer matrix and thus degrade the mechanical properties of the composite but large enough to effectively reinforce the substrate. Typically, the weight ratio of substrate to reinforcement is from about 90:10 to about 10:90 with more preferred materials having a ratio of from about 80:20 to about 20:80.

The composites may contain additional materials as well, as long as these additional materials are nontoxic and biocompatible and have physical and degradation properties consistent with the intended uses of these composites in erodible implants. Therefore, these composites could contain pharmaceutically acceptable plasticizers, mold release agents, radioimaging materials, or the like. Other materials can be present as well, including excipients to promote or regulate erosion and degradation, and pharmaceutically active materials such as bone growth factors, drugs such as antibiotics or the like.

The composites are typically formed by admixing the reinforcement, which is most commonly in a loose fiber form but which could also be in the form of fabrics, felts, or the like, if desired and if compatible with the properties of the reinforcement, with the substrate polymer or a polymer precursor in a fluid state. This material can them be cast into shapes desired for medical reinforcement applications or it can be cast into billets from which the desired shapes can be machined. Alternatively the substrate and fiber can be dry-mixed and formed into the desired shapes by injection molding, hot-pressing, transfer molding and the like. The actual forming techniques employed are known in the art and will depend upon whether the polymer is thermoplastic or thermorigid and also will depend upon whether it is the polymer itself which is being formed or rather a fluid precursor which is then solidified by curing or the like.

The final form of the reinforcements produced according to the invention can include the various shapes described heretofore for medical reinforcement purposes. These shapes include, without limitation, rods, pins, screws, plates and the like.

DESCRIPTION OF PREFERRED EMBODIMENTS

This invention will be further described by the following examples and representative preparations. These are presented to exemplify the practice of this invention and are not to be construed as limiting its scope.

A study was carried out investigating the suitability of poly(ortho esters) as composite substrates and the suitability of CSM as a composite reinforcement. The polymer investigated was linear poly(ortho ester) (POE) prepared from 3,9-bis-(ethylidene 2,4,8,10-tetraoxaspiro[5.5]-undecane) and a 60:40 mole ratio of rigid trans-cyclohexanedimethanol and flexible 1,6-hexane-diol. Equivalent, and sometimes superior, results were achieved with the same system and a 90:10 ratio of these alcohols.

A typical preparation of a test quantity of a CSM-reinforced POE composite is as follows:

1. CSM Fiber Preparation—Removal of Impurities add 25 g of calcium-sodium metaphosphate (CSM) fibers (Monsanto) to a 1000 ml beaker with a stirring bar add 500 ml of deionized water and boil for 4 hours, maintain volume level of water as needed filter the hot suspension with a Buchner funnel under vacuum wash fibers with room temperature deionized water dry in a vacuum oven at 90°-100° C. for 24 hours.

2. Modification of CSM Fiber Surface

Since the raw fiber surface is slightly acidic and the rate of hydrolysis of poly(ortho ester) (POE) increases with increasing acidity, it is preferred to create a basic fiber surface. To make the CSM fiber more compatible with the POE polymer a basic coupling agent, such as a diamine silane (Dow Corning, Z-6020) may be bonded to the CSM fiber surface. This may be carried out as follows:

in a 250 ml beaker add 99.7 ml of methanol (EM Science, OmniSolv) and 0.3 ml of the diamine silane (Dow Corning, Z-6020) to produce a 0.3% solution by volume slowly add 25 g of washed CSM fibers to the above solution and stir, using a magnetic stirring bar, until a slurry is formed filter the above suspension with a Buchner funnel under vacuum dry the residue in an oven for 3.5 hours at 90°–10020 C. using an air flow, to cure the coupling agent to the fiber cool to room temperature and sieve the sized fibers through a 100 mesh Tyler sieve screen using a Rototap solvent wash the sized fibers with methanol to remove residual coupling agent dry sized fibers in a vacuum oven at 90°–100° C. for several hours.

Pretreatment of Poly(ortho ester) Polymer

A linear ortho ester polymer (POE) is prepared from 3,9-bis-(ethylidene 2,4,8,10-tetraoxaspiro[5.5]-undecane) and a 60:40 mole ratio of rigid trans-cyclohexanedimethanol and flexible 1,6-hexane-diol using the general methods set forth in the examples of U.S. Pat. No. 4,304,767. One of the several repeat preparations is carried out as follows:

Into a 5-L, three-necked flask equipped with an overhead stirrer, an argon inlet tube and a condenser are placed 86.54 g (0.60 mole) trans-cyclohexanedimethanol and 47.33 g (0.40 mole) 1,6-hexanediol and 1.8 L of distilled tetrahydrofuran. The mixture is stirred until all solids have dissolved; then 212.31 g (1 mole) of 3,9-bis(ethylidene 2,4,8,10-tetraoxaspiro [5.5] undecane) is added. The polymerization is initiated by the addition of 2 ml of a solution of p-toluenesulfonic acid (20 mg/ml) in tetrahydrofuran.

The polymerization temperature rapidly rises to the boiling point of tetrahydrofuran, then gradually decreases. Stirring is continued for about 2 hr., 10 ml of triethylamine stabilizer added, and the reaction mixture then very slowly poured with vigorous stirring into about 15 gallons of methanol containing 100 ml of triethylamine.

The precipitated polymer is collected by vacuum filtration and dried in a vacuum oven at 60° C. for 24 hrs. The weight of the dried polymer was 346.03 (98.8% yield). The molecular weight determined by light scattering was 95,300.

To make a 90/10, use 129.81 g (0.90 mole) trans-cyclohexanedimethanol, 11.83 (0.10 mole) 1,6-hexanediol and 212.31 g (1 mole) 3,9-bis (ethylidene 2,4,8,10-tetraoxaspiro [5,5] undecane).

mill the POE polymer through a 40 mesh screen using a Thomas Wiley Mill (Thomas Scientific)

as a precaution after milling, dry the milled polymer in a vacuum oven at 50° C. for 24 hours before using.

4. Preparation of Composites

Mixing of the powdered POE polymer and the sized CSM fibers is achieved by simply dry-mixing the appropriate amounts of fiber and polymer depending on the desired fiber loading.

For example to prepare 5 composite samples, at a fiber-volume fraction equal to 30%, for flexure testing according the ASTM Standard D-790 for procedure and sample size, the following steps are carried out:

in a narrow diameter bottle (dia=2") add 2.85 g of sized CSM fibers sprinkle in a milled POE polymer, 3.15 g total, while blending the fibers with the impeller of a stirring assembly use low to medium speed.

5. Hot-Pressing of Composites set and heat the platens of a Carver Press to 150° C.

fill the steel die with 1.20 g of the drymixed composite transfer the die into the space between the platens and apply 500 lbs-f as a preload insert the thermocouple temperature probe into the die heat the die to 130° C.

when the die temperature reaches 130° C. apply 2000 psi to the mold the temperature and pressure will remain constant after 5 minutes turn on the cold water to cool the platens and the die; make sure the pressure is at 2000 psi when the die temperature decreases to 45° C. or less shut off the water, release the pressure and remove the mold and sample this yields a composite sample 1½"×½"×1/16" which is ready for flexure testing.

Similar processing with other substrates such as other ortho esters or ortho esters having differing ratios of diols, say 90:10 instead of 60:40, or with other types of substrate or reinforcement would yield similar products.

Testing of Materials

Acute toxicity screening was performed on ethylene oxide sterilized samples. Cytotoxicity was determined by agar overlay assay of direct samples. USP Toxicity Class VI tests (systemic and intracutaneous injection of extracts, 37° C. for 9 hours) and USP Implantation XXI tests (intramuscular implantation, followed by gross and macroscopic examination) were conducted.

Flexural modulus and flexural strength were measured in accordance with ASTM Standard D 790-81 (3 pt. bend). Specimens were immersed in Tris-buffered saline, pH 5.0 and 7.4 (aerated), at 37° C. and tested after 1, 3, and 6 weeks exposure. Another set of specimens was irradiated with 2.5 Mrad of gamma radiation and exposed to aerated Tris-buffered saline, pH 7.4, at 37° C. All mechanical testing was performed in triplicate.

Figure 2:
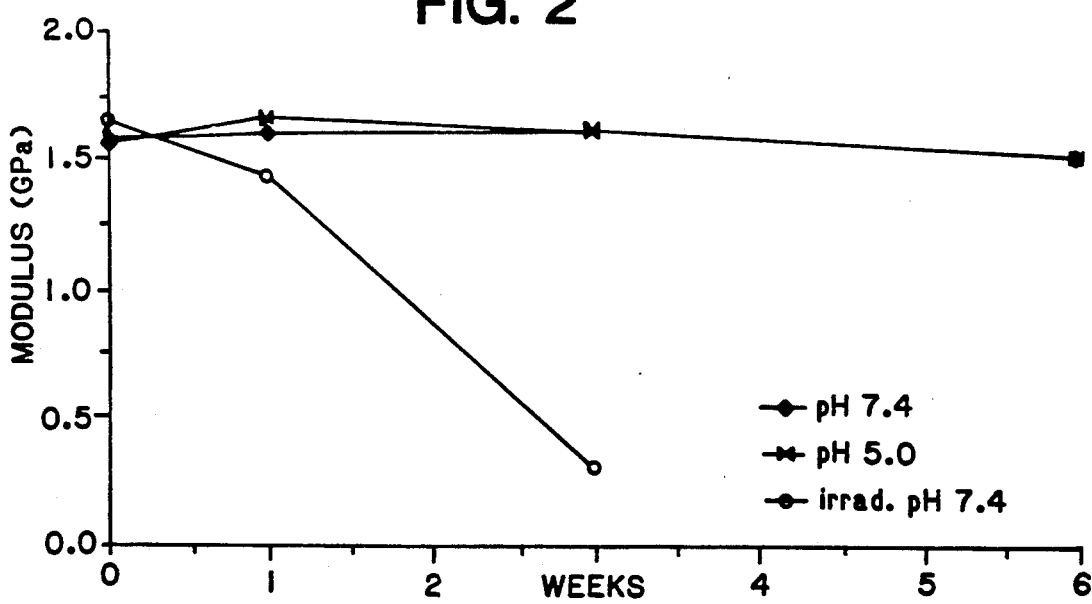
FIG. 2 is a graph illustrating the degradation of certain composites of this invention in simulated internal media as determined by measuring flexural modulus.
Figure 6A:
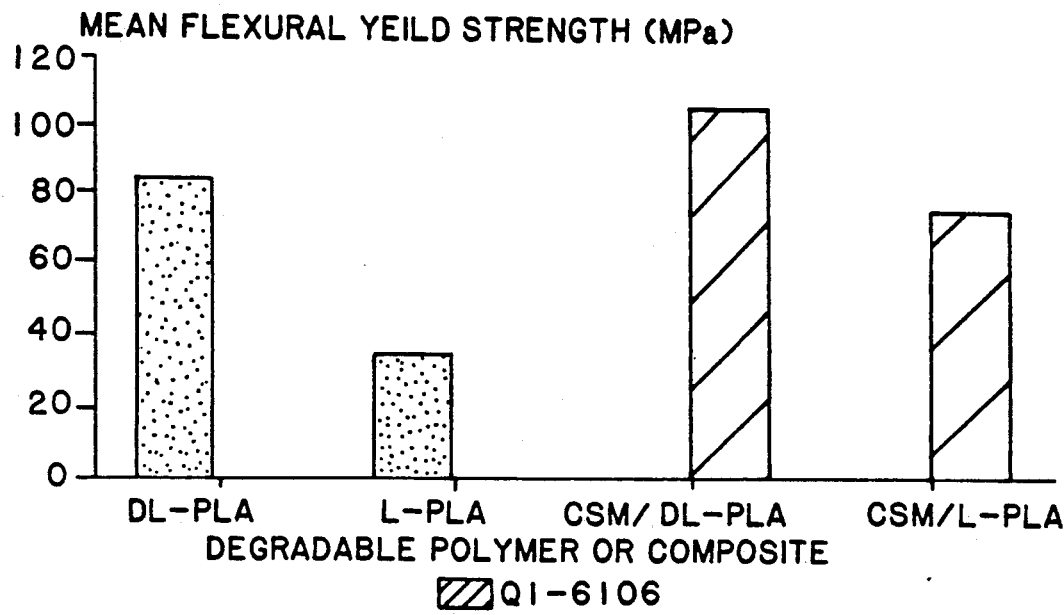
FIGS. 6a and 6b are bar graphs illustrating the improvement in properties of poly(lactic acid) materials achieved with reinforcement.
Figure 6B:
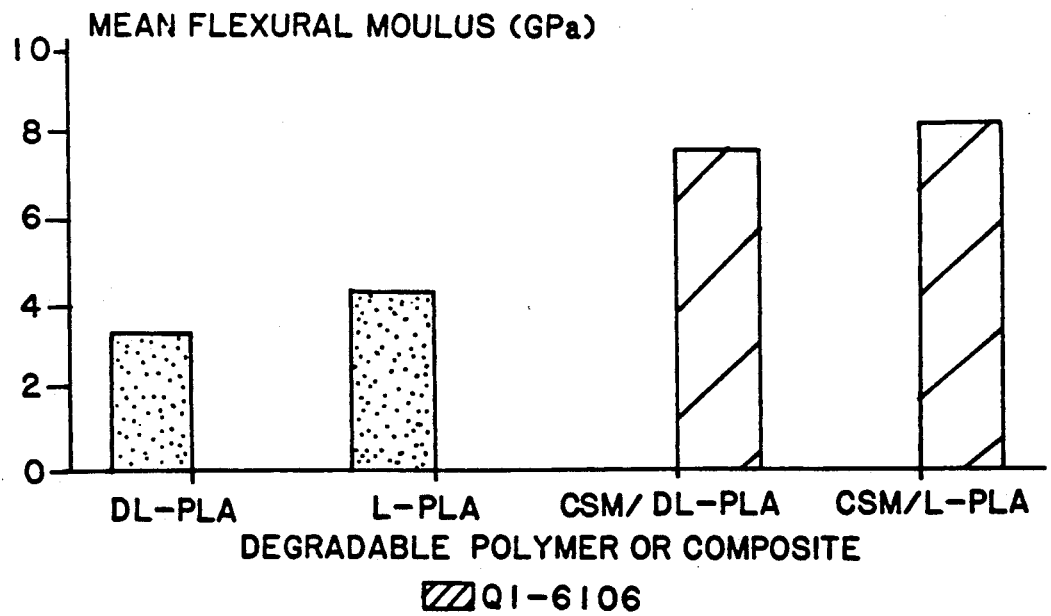

Cytotoxicity, toxicity, and implantation tests indicated that 60:40 POE is non-toxic, with test responses comparable to negative controls. The initial flexural strength and modulus were 65 MPa and 1.6 GPa. The effects of exposure to saline, pH 5.0 and 7.4, at 37° C. are shown in FIGS. 1 and 2. POE retained approximately 90% of its initial flexural strength and modulus at 6 weeks in vitro, and the two pH levels produced no significant difference in the rate of mechanical property degradation. Radiation sterilization reduced initial flexural strength by 60%, had a negligible effect on initial modulus, and markedly increased the degradation rate.

POE shows low toxicity and retains excellent mechanical properties for 6 or more weeks in vitro. Radiation sterilization appears to severely compromise its mechanical properties.

Additional studies detailed the initial histological and mechanical properties of the following biodegradable polymer composites: poly(ortho ester) (POE) and copolymers of epsilon-caprolactone/L-lactide (CLLA), in 90:10 and 10:90 ratios, reinforced with degradable glassy sodium-calcium-aluminum-polyphosphate (NCAP) and crystalline calcium-sodium-metaphosphate (CSM), in the form of randomly oriented short fibers.

NCAP fiber and CSM fiber samples were submitted for acute toxicity screening by standard Tissue Culture Agar Overlay Assay (cytotoxicity), USP Class VI (systemic and intracutaneous toxicity) and USP XXI (intramuscular implantation) protocols.

Six composite types were prepared by reinforcing each of 3 polymers (CLLA 10:90, CLLA 90:10 and POE) with either NCAP or CSM fibers and were implanted into New Zealand Rex rabbits to assess the effect of materials on both muscle and bone. ASTM Standards, F496-78 and F361-80 were adopted for muscle and bone implant methodology respectively. Animals were sacrificed at 4, 12 and 26 weeks with standard histological analysis performed on retrieved implant/tissue specimens.

Parallel in vitro mechanical degradation studies were performed by immersing composite samples in phosphate buffered saline, pH 7.4, at 37° C., for periods of 6, 12 and 26 weeks. Tensile and compressive mechanical properties were determined in triplicate for each exposure period.

Both NCAP and CSM fibers were rated nontoxic in the cytotoxicity, systemic and intracutaneous toxicity and intramuscular implantation. Responses were comparable to negative controls.

After muscle implantations, necrotic foci were observed in 12 of 22 NCAP-containing specimens, while only 2 of 14 CSM-containing specimens and 2 of 11 CLLA 90:10 copolymer specimens showed necrosis. However, the necrosis was localized and associated with the fibrous capsule. None of the implanted sites exhibited the uniform zone associated with gross leeching of toxic substances from the implant material.

Bone histologic examination revealed a mild proliferation of fibrous connective tissue on the periosteal surface for all specimens. This tissue varied in thickness and contained lymphocytes and macrophages. The bone showed no evidence of necrosis or toxicity.

All in vivo and in vitro samples were sterilized with 2.5 MRads of gamma radiation prior to usage. All of the samples containing NCAP fibers showed some discoloration after irradiation, and therefore possibly some degradation.

FIGS. 3a and 3b show compressive strength and stiffness after in vitro exposure. CLLA 10:90 and POE polymers with NCAP fibers started out much stiffer and stronger than the rest, but degraded quickly.

FIGS. 4a and 4b show tensile strength and stiffness after in vitro exposure. Both CLLA 10:90/NCAP and POE/CSM started out with relatively high stiffness and strength, but only POE/CSM retained significant strength at 6 and 12 weeks. CLLA 10:90/NCAP had the highest modulus initially, but at 6 weeks, POE/CSM was several times stiffer than all other materials.

Other results of mechanical tests on pure ortho ester and lactic acid sustrates and reinforced composites based on these substrates are presented in FIGS. 5a, 5b, 6a and 6b. These results show that the CSM fibers effectively reinforce both systems and that treating the CSM surface with silane coupling agent improves composite integrity with the poly(lactic acid) materials and with the POE materials.

What is claimed is:

1. A reinforced bioerodible composite having a polymer substrate phase and dispersed therethrough a fiber reinforcement phase in a weight ratio of said polymer substrate phase to said fiber reinforcement phase of from 10:90 to 90:10, said polymer substrate phase being selected from the group consisting of poly(ortho ester), poly(levo lactic acid), poly(d/l lactic acid), poly(glycolic acid), the poly(ethyl ether) polydioxanone, L-lactide, epsilon-caprolactone, polycaprolactone, polyanhydrides, polypropylene fumarate, polyiminocarbonate, polyhydroxybutrate, polyhydroxyvalerate, poly(alkylene oxalate) and poly(ester-amide) and mixtures and copolymers thereof and said fiber reinforcement phase being selected from the group consisting of calcium-sodium metaphosphate, calcium phosphate, oriented poly(glycolic acid), oriented poly(lactic acid), sodium-calcium-aluminum polyphosphate, and mixtures thereof, subject to the proviso that when said polymer substrate phase is other than poly(ortho ester), said fiber reinforcement phase must include calcium-sodium metaphosphate and that when said fiber reinforcement phase is other than calcium-sodium metaphosphate, said polymer substrate phase must include poly(ortho ester).

2. The reinforced bioerodible composite of claim 1 wherein the polymer substrate phase is a poly(ortho ester) of polyols and ketene acetals each having a functionality of two or more.

3. The reinforced bioerodible composite of claim 2 wherein the poly(ortho ester) has the formula

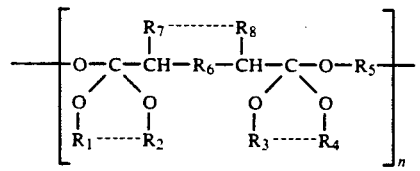

wherein n is an integer substantially greater than 10; wherein $R_1$, $R_2$, $R_3$ and $R_4$ are the same or different essentially hydrocarbon groups, $R_1$ and $R_2$ being separate groups or parts of a cyclic group and $R_3$ and $R_4$ being separate groups or parts of a cyclic group; $R_5$ is an essentially hydrocarbon group which is the residue of a polyol $R_5(OH)_n$ wherein n is an integer equal to two or more, such polyol being a single molecular species or a mixture of molecular species; $R_6$ is a valence bond or an essentially hydrocarbon group; $R_7$ and $R_8$ are hydrogen or essentially hydrocarbon groups which may be separate groups or may form parts of a cyclic group; and wherein such linear chains may be crosslinked to similar chains.

4. The reinforced bioerodible composite of claim 2 wherein the poly(ortho ester) has the formula

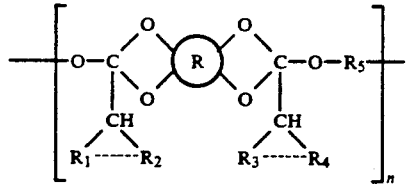

wherein n is an integer substantially greater than 10; wherein $R_1$ and $R_2$ are hydrogen or the same or different essentially hydrocarbon groups and may be separate groups or may form parts of a cyclic group; ⓡ is a quadrivalent organic grouping; $R_3$ and $R_4$ are hydrogen or the same or different essentially hydrocarbon groups and may be separate groups or may form parts of a cyclic group; $R_5$ is an essentially hydrocarbon group which is the residue of a polyol $R_5(OH)_a$ wherein a is an integer equal to two or more, such polyol being a single molecular species or a mixture of molecular species; and wherein such linear chain may be crosslinked with other similar chains.

5. In a medical implant for use within the body and formed of a reinforced bioerodible composite capable of undergoing bioerosion within the body, the improvement comprising employing as said reinforced bioerodible composite a material of claim 1.

6. In a medical implant for use within the body and formed of a reinforced bioerodible composite capable of undergoing bioerosion within the body, the improvement comprising employing as said reinforced bioerodible composite a material of claim 1.

7. In a medical implant for use within the body and formed of a reinforced bioerodible composite capable of undergoing bioerosion within the body, the improvement comprising employing as said reinforced bioerodible composite a material of claim 2.

8. In a medical implant for use within the body and formed of a reinforced bioerodible composite capable of undergoing bioerosion within the body, the improvement comprising employing as said reinforced bioerodible composite a material of claim 3.

9. In a medical implant for use within the body and formed of a reinforced bioerodible composite capable of undergoing bioerosion within the body, the improvement comprising employing as said reinforced bioerodible composite a material of claim 4.

10. In a medical implant for use within the body and formed of a reinforced bioerodible composite capable of undergoing bioerosion within the body, the improvement comprising employing as said reinforced bioerodible composite a material of claim 1.

* * * * *